(12) United States Patent
Gérard et al.

(10) Patent No.: US 11,904,317 B2
(45) Date of Patent: Feb. 20, 2024

(54) MICROFLUIDIC METHOD FOR SINGLE CELL ANALYSIS

(71) Applicant: HIFIBIO SAS, Paris (FR)

(72) Inventors: Annabelle Patricia Veronique Gérard, Palaiseau (FR); Vera Menrath, Saint Cyr sous Dourdan (FR)

(73) Assignee: HIFIBIO SAS, Paris (FR)

( * ) Notice: Subject to any disclaimer, the term of this patent is extended or adjusted under 35 U.S.C. 154(b) by 658 days.

(21) Appl. No.: 17/047,545

(22) PCT Filed: Apr. 18, 2019

(86) PCT No.: PCT/EP2019/060210
§ 371 (c)(1),
(2) Date: Oct. 14, 2020

(87) PCT Pub. No.: WO2019/202135
PCT Pub. Date: Oct. 24, 2019

(65) Prior Publication Data
US 2021/0146366 A1    May 20, 2021

(30) Foreign Application Priority Data
Apr. 18, 2018 (EP) .................................... 18168084

(51) Int. Cl.
*B01L 3/00*  (2006.01)
*G01N 33/543*  (2006.01)
*G01N 33/569*  (2006.01)

(52) U.S. Cl.
CPC .. *B01L 3/502784* (2013.01); *G01N 33/54366* (2013.01); *G01N 33/569* (2013.01); *B01L 2200/0652* (2013.01); *B01L 2200/16* (2013.01); *B01L 2400/02* (2013.01); *G01N 2458/00* (2013.01)

(58) Field of Classification Search
None
See application file for complete search history.

(56) References Cited

U.S. PATENT DOCUMENTS

2013/0052648 A1* 2/2013 Yarmush ............ G01N 15/1484
435/6.12
2017/0307626 A1 10/2017 Griffiths et al.

FOREIGN PATENT DOCUMENTS

CN          107110854 A    8/2017

OTHER PUBLICATIONS

Agresti et al., Ultrahigh-throughput screening in drop-based microfluidics for directed evolution, 2010, PNAS, vol. 107, 4004-4009 (Year: 2010).*

(Continued)

*Primary Examiner* — Christine T Mui
*Assistant Examiner* — Kathryn Elizabeth Limbaugh
(74) *Attorney, Agent, or Firm* — McCarter & English, LLP; Yu Lu; James M. Alburger

(57) ABSTRACT

A first aspect of the present invention is directed to a method for the detection of a compound of interest in a microfluidic system. A second aspect of the present invention relates to the use of the method according to the first aspect for monitoring a biological event. A further aspect of the present invention is directed to a microfluidic system and the use thereof for carrying out the method according to the first aspect.

15 Claims, 13 Drawing Sheets

○ Cytokine secreting cell
⨉ Cell surface antibody conjugated to a-cytokine antibody (capture reagent)
⨉ Fluorescent a-cytokine (detection reagent)
<u>Is COFLOWED in droplet</u>
✧ Secreted cytokine

(56) References Cited

OTHER PUBLICATIONS

Eyer, K., et al, "Single-cell deep phenotyping of IgG-secreting cells for high-resolution immune monitoring", Nature Biotechnology, vol. 35, No. 10, Sep. 11, 2017 (Sep. 11, 2017), p. 977-982.
Mazutis, L., et al, "Single-cell analysis and sorting using droplet-based microfluidics", Nature Protocols, vol. 8, No. 5, Apr. 4, 2013 (Apr. 4, 2013), p. 870-891.

* cited by examiner

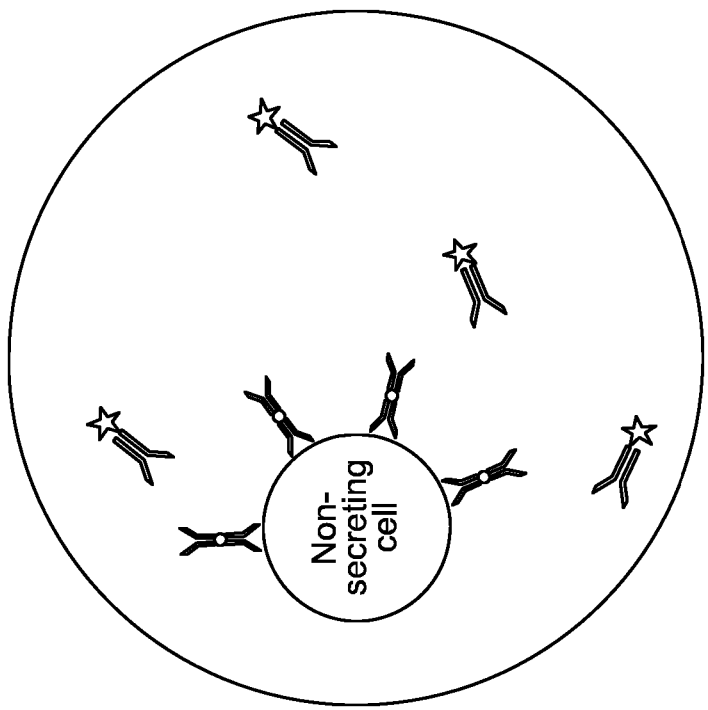
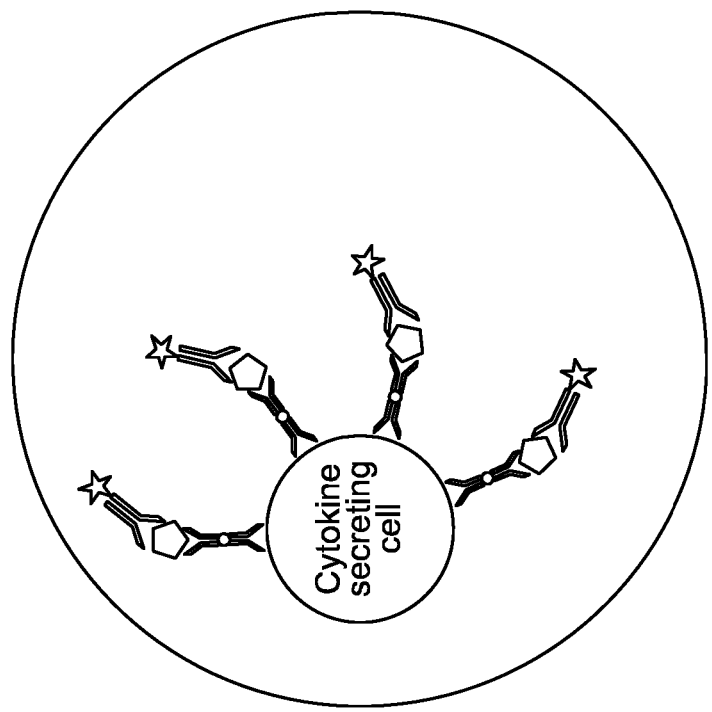
FIG. 1B
○ Cytokine secreting cell
✗ Cell surface antibody conjugated to a-cytokine antibody (capture reagent)
✭ Fluorescent a-cytokine (detection reagent) *Is COFLOWED in droplet*
⬠ Secreted cytokine
FIG. 1A

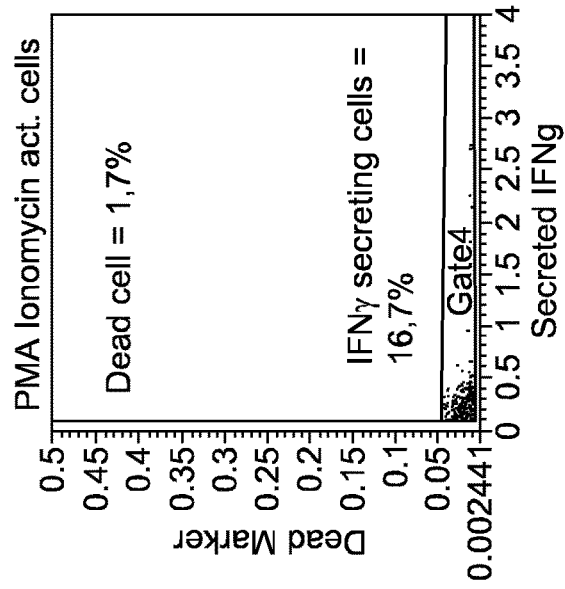
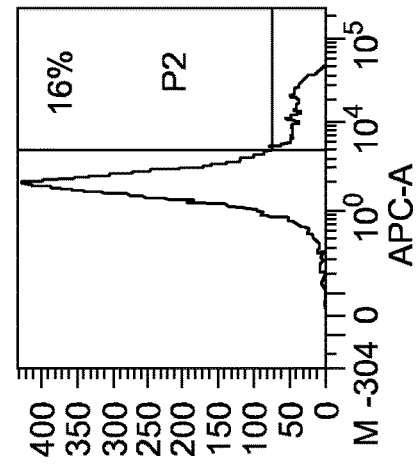
FIG. 2A
FIG. 2B
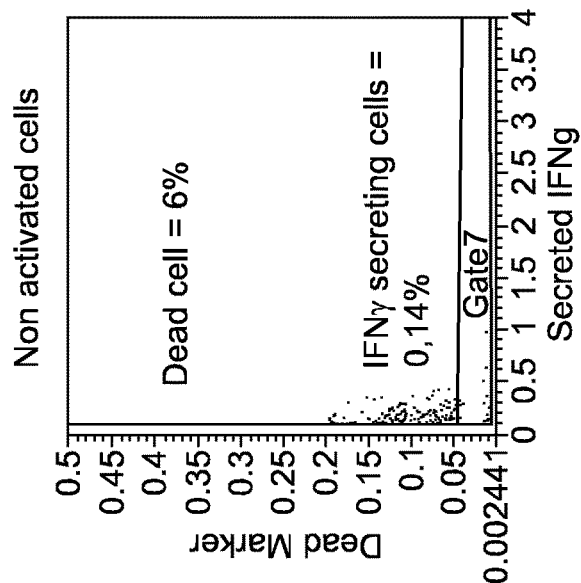
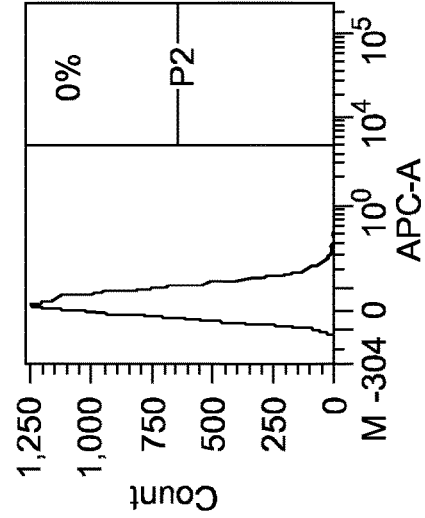

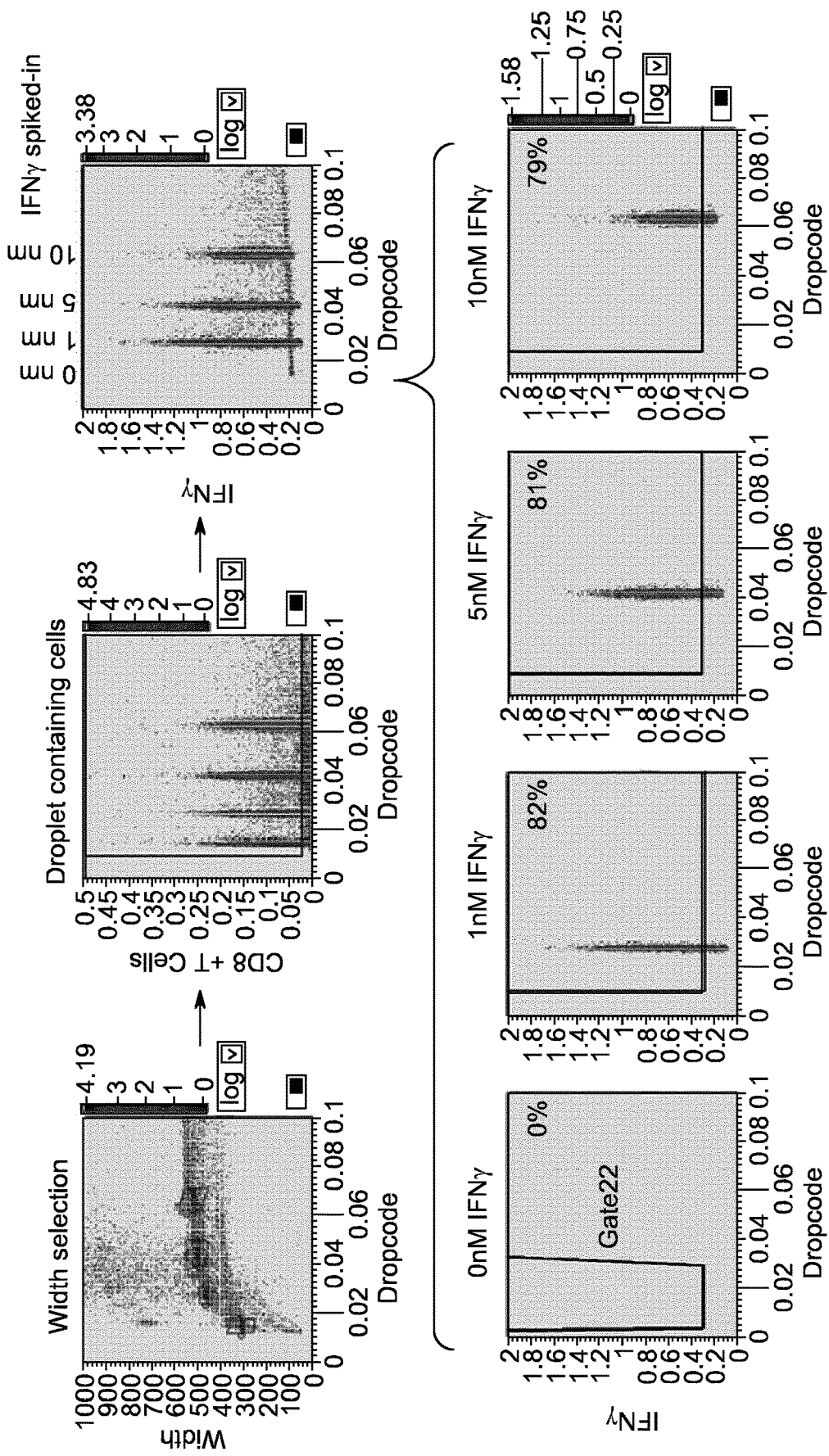

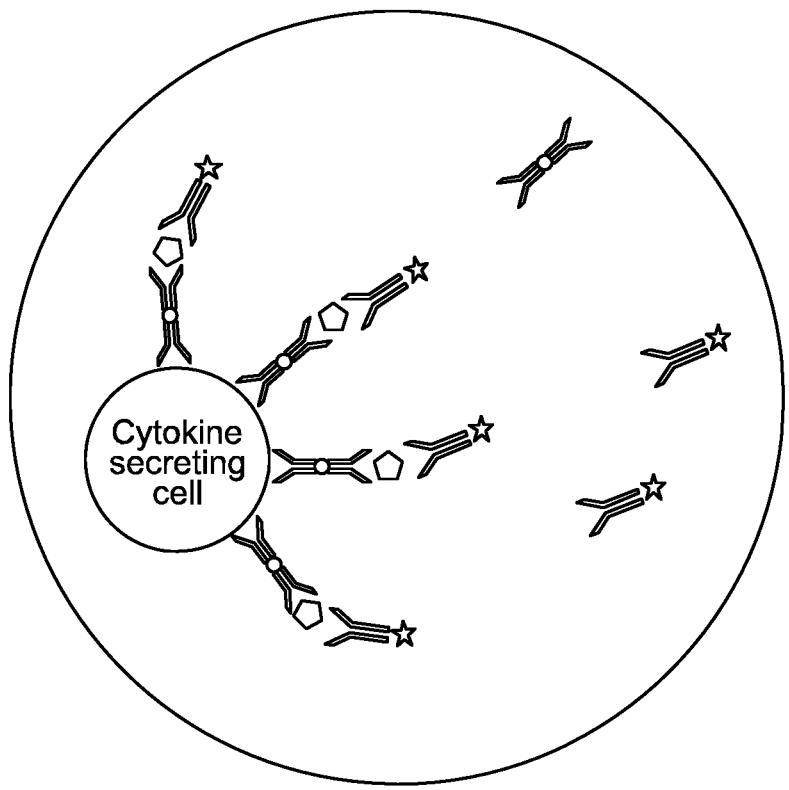
 Cytokine secreting cell
 Cell surface antibody conjugated to a-cytokine antibody (capture reagent)
*Is COFLOWED in droplets*
 Fluorescent a-cytokine (detection reagent)
*Is COFLOWED in droplets*
 Secreted cytokine
FIG. 5B

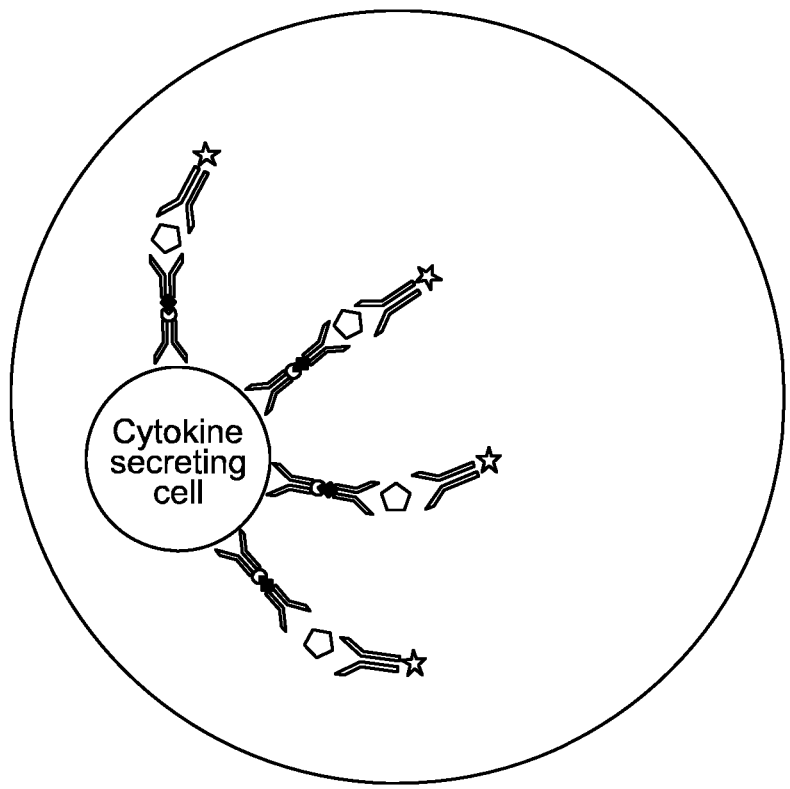
| | |
|---|---|
| ◯ | Cytokine secreting cell |
| 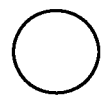 | Cell surface antibody conjugated to a-cytokine antibody (capture reagent) composed of: |
|  | Antibody specific to cell surface conjugated with ligand A |
| ⇐ | Antibody specific to cytokine conjugated with ligand B |
|  | Fluorescent a-cytokine (detection reagent) *Is COFLOWED in droplets* |
|  | Secreted cytokine |
FIG. 5C

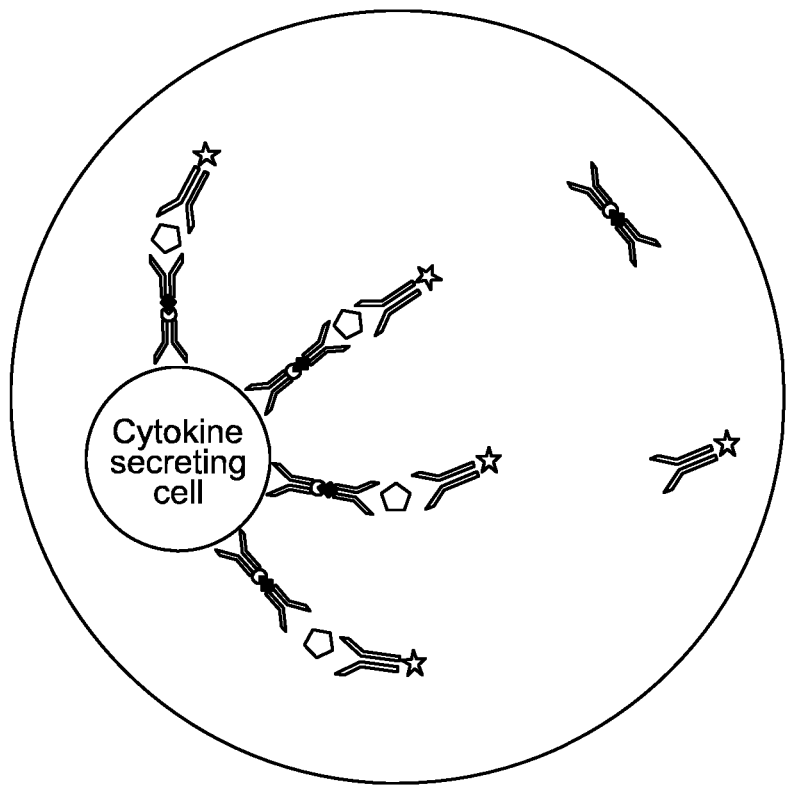
| | |
|---|---|
| ◯ | Cytokine secreting cell |
| 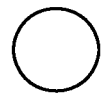 | Cell surface antibody conjugated to a-cytokine antibody (capture reagent) composed of: |
|  | Antibody specific to cell surface conjugated with ligand A |
|  | Antibody specific to cytokine conjugated with ligand B |
|  | Fluorescent a-cytokine (detection reagent) *Is COFLOWED in droplets* |
|  | Secreted cytokine |
FIG. 5D

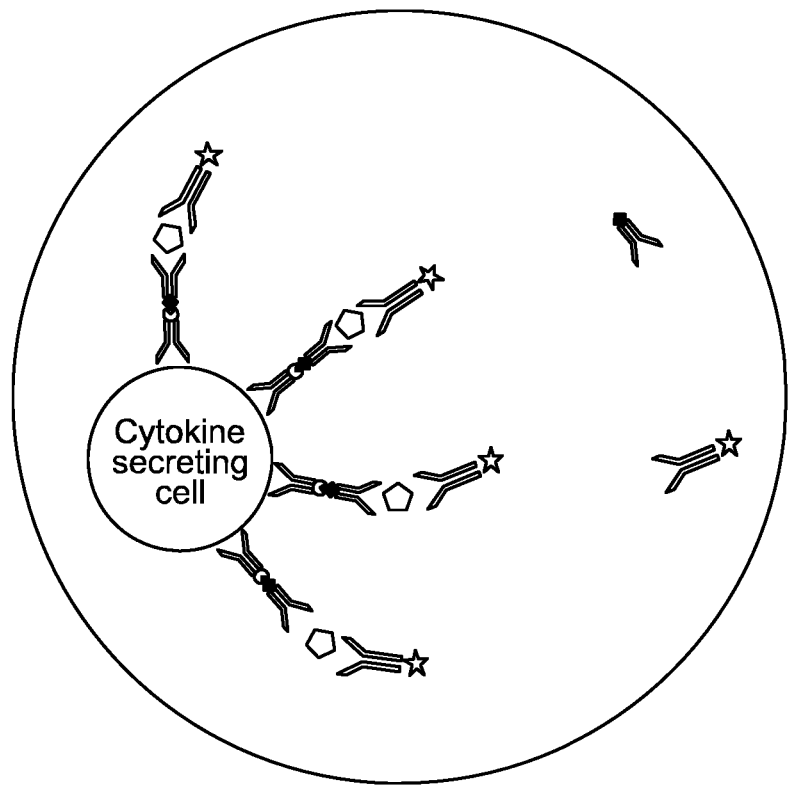

◯ Cytokine secreting cell

 Cell surface antibody conjugated to a-cytokine antibody (capture reagent) composed of:

 Antibody specific to cell surface conjugated with ligand A
*Is bound to the cell (pre-incubation)*

 Antibody specific to cytokine conjugated with ligand B
*Is COFLOWED in droplets*

 Fluorescent a-cytokine (detection reagent)
*Is COFLOWED in droplets*

 Secreted cytokine

FIG. 5E

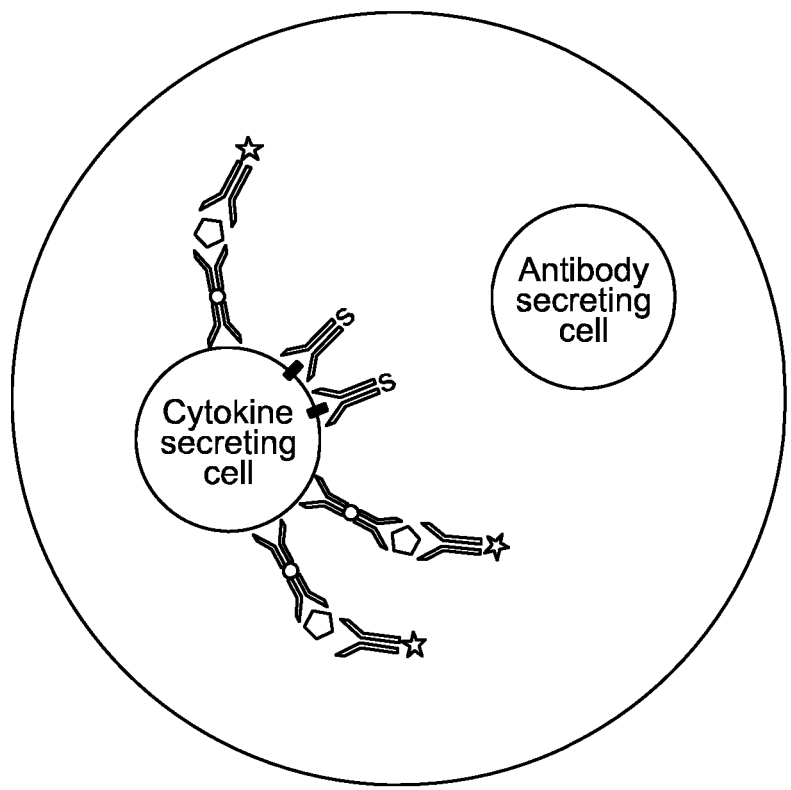
| | |
|---|---|
|  | Cytokine factors or antibody secreting cell |
| 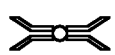 | Cell surface antibody conjugated to a-cytokine antibody (capture reagent) |
|  | Fluorescent a-cytokine (detection reagent) *Is COFLOWED in droplets* |
|  | Secreted cytokine |
|  | Receptor or Tcell surface |
|  | Secreted antibody specific to receptor on T cell surface |
FIG. 6

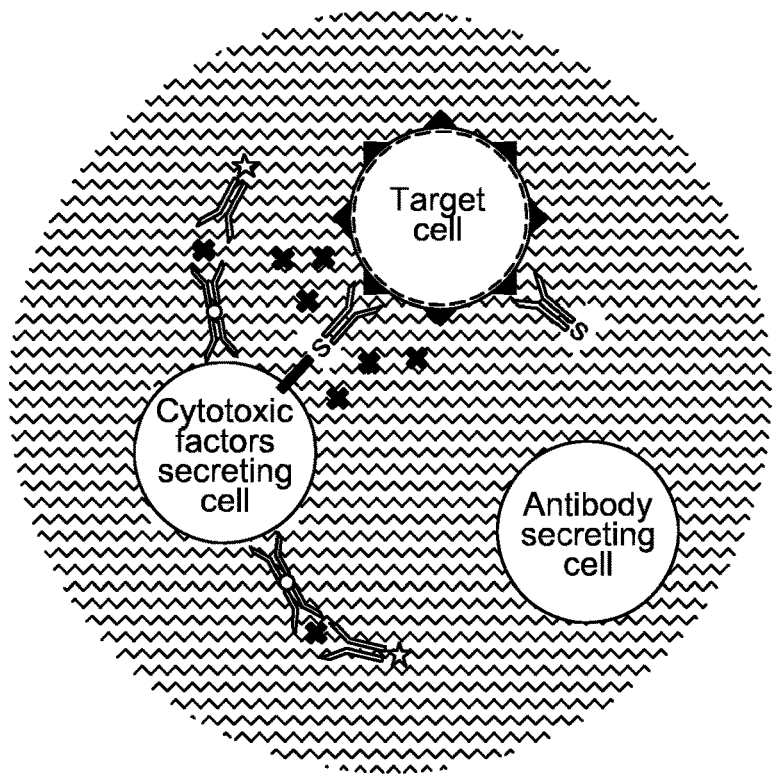

| | Droplet containing released compound from the dying target cell |
|---|---|
| ◯ | Cytokine factors or antibody secreting cell |
| (◯) | Dying target cell |
| ⇒o⇐ | Cell surface antibody conjugated to a-cytotoxic factors antibody (capture reagent) |
| ⇒☆ | Fluorescent a-cytokine (detection reagent) *Is COFLOWED in droplets* |
| ✖ | Secreted cytotoxic factors |
| ▲ | Antigen of interest on target cell membrane |
| ⇒s | Secreted target-specific antibody |
| — | Fc receptor |

FIG. 7

MICROFLUIDIC METHOD FOR SINGLE CELL ANALYSIS

CROSS-REFERENCE TO RELATED APPLICATIONS

This application is a national state filing under 35 U.S.C. § 371 of International Application No. PCT/EP2019/060210, Filed Apr. 18, 2019, which claims the benefit of and priority to European Patent Application No. 18168084.4, filed on Apr. 18, 2018, the contents of all of which are incorporated by reference herein in their entirety. International Application No. PCT/EP2019/060210 was published under PCT Article 21(2) in English.

FIELD OF THE INVENTION

The present invention is in the field of cellular and molecular biology and is based on methods for detecting a compound of interest produced by a single cell in a droplet. The invention is also related to the field of microfluidics and encompasses microfluidic devices and their use thereof for carrying out biological assays.

BACKGROUND

During a drug discovery program, one of the step is related to the validation of the drug candidate based on its expected biological effect. On that purpose, either in-vivo or in-vitro models can be used. On one hand, in-vivo experiments have the advantage to address the question on a whole living organism. However, animal models are not necessarily predictive of what would happen in human. Moreover, in-vivo studies are expensive and their use is limited by ethical considerations. On the other hand, in-vitro systems, even though failing to replicate the precise cellular conditions of an organism, can be performed on human cells and are particularly suitable in case of screening process, where a high throughput is needed. These cell-based assays are usually performed in bulk on cells of interest. However, in certain conditions, as it is the case for immune cells, each of them is unique and the need of functional cell-based assays at a single cell level is of great interest. Indeed, measuring immune responses in bulk populations increases the risks to mask the unique behavior or contribution of each single cell, especially when immune response is highly heterogenous, or driven by rare cell populations. Therefore, a single cell-based assay is required to better understand potential variations from cell to cell that would consider individual cell phenotypes.

Recent advances in single cell analysis methods have improved biological understandings within single cells by characterizing relationships between cells within a population. Therefore, by determining rare cell events or small changes between individual cells it is possible to address unresolved questions in the field of cancer, immunology, infectious disease, stem cell and developmental biology and neurology.

Immune cells protect the host organism against diseases by producing antibodies, chemokines and cytokines. This former class of molecules are group of proteins secreted by innate and adaptive immune cells acting as chemical messengers. Their production by immune cells is due to the body's ability to raise an immune response and therefore has high clinical diagnostic value. Thus, both the study of antibody and cytokine secretion kinetic could give significant information for diagnostics of diseases and personalized therapies.

However, the absence of quantitative, single cell, high-throughput systems to analyze individual secreting cells limits investigation on dynamics of the immune response.

Recently, droplet based microfluidic systems have attracted significant interest because of their range of applications towards cell biology and based on their ability to control the mechanical, biological and fluidic environment at the single cell level. The technology enables assays to be carried out very rapidly (up to thousands of cells and/or droplet per second). Additionally, the system provides macroscale (pico- or nanoliter volumes of samples and reagents) cell culture experiments where biological samples are confined in droplets, allowing fast detection of high concentration of compound (from pM to µM range). Moreover, the system minimizes sample loss and cross contamination but allows fast mixing, thermal transfer, and chemical reaction. Interestingly, the technology provides the possibility to perform large-scale genotypic and phenotypic screens at the single cell level.

In the last few years, different microfluidic devices and systems have been proposed for single-cell analysis (Gross et al. 2015, Int. J. Mol. Sci. 16(8):16897-16919; Reece et al. 2016, Curr. Opin. Biotechnol. 40:90-96).

Different methods and techniques have been proposed for cells sorting in microfluidics. Sorting principles are mainly classified in two categories: methods based on physical properties of the cells, such as size, deformability, electric or optical properties, and methods based on biomolecular properties, notably specific surface antigens.

High purity cell separation and sorting can be achieved using a monoclonal antibody that binds to a cellular component. Widely used antibody-based cell analysis and/or separation techniques include cell panning, magnetic cell sorting (MACS) and fluorescence-activated cell sorting (FACS), including fluorescence-activated droplet sorting (FADS).

In cell panning technique, cells exhibiting specific antigens can be selectively attached on an antibody-coated surface. Despite this technique can provide high purity, it is affected by some limitations such as high cell loss or impact on cell viability.

In other cell panning technique as single cell sorting by flow cytometry, cells secreting specific molecules can be selectively captured by an antibody bound either to cell surface or to an extra cellular matrix (Campbell et al., 2010 J. Immunol. 185:28-32; Manz et al., 1995, Proc. Natl. Acad. Sci. USA 92:1921-1925) like an antibody-coated surface. Despite this technique can detect secreted molecules, at the single cell level when coupled to a flow cytometer, it is affected by some limitations such as high background due to cell concentration (thus impacting cell purity) and lack of quantitative separations based on secretion and lack of real time quantitative secretion rate measurement.

MACS employs antibody-conjugated magnetic beads to capture specific antigens on the cell surface. Cell populations labeled with magnetic beads can be selectively collected under a magnetic field produced by a permanent magnet. MACS allows significantly higher throughput but no single cell sorting and lower purity than FACS. Another notable limitation is the difficulty of detachment and removal of the beads after separation, which may prevent subsequent analysis.

Another exemplary of cell separation is using microfluidic method based on the use of magnetic beads particles, used as a beadline. The method is disclosed in international patent application WO 2016/059182 A1, wherein each droplet is characterized by the presence of an aggregate of particles forming a column of magnetic beads intended to detect the occurrence of a secreted molecule by means of a system of capturing said molecules onto the beadline and detecting elements onto said beadline. The advantage of the method proposed in WO 2016/059182 A1 is to be able to assess at the single cell level secreted molecules. However, the method disclosed in WO 2016/059182 A1 is dependent from the presence of the particle aggregate and thus prevent sophisticated assays requiring several cells within the same compartment. The assays suffer from intrinsic flexibility limitations. In addition, the sensitivity is intrinsically limited by the binding capacity of the particles aggregates.

In general, limitations affecting currently available methods for analyzing and/or separating single cells based on secreted molecules include poor efficiency or low yield/recovery, degradation of cell viability/functionality in the separation process, poor reliability, poor flexibility and/or low throughput in terms of single cells isolated per second. Therefore, it is evident that an improved microfluidic method for analyzing and separating compound-secreting single cell is highly required to address the above-mentioned issues.

SUMMARY OF THE INVENTION

A first aspect of the present invention is directed to a method for the detection of a compound of interest in a microfluidic system comprising the steps of:
 a. creating at least one droplet in said microfluidic system, said at least one droplet comprising:
  i. at least one single cell,
  ii. one or more first capturing agent, wherein said one or more first capturing agent is capable of binding said at least one single cell as well as said compound of interest,
  iii. one or more second capturing agent comprising a label, wherein said one or more second capturing agent is capable of binding said compound of interest,
 b. incubating said at least one droplet capable of generating a detectable event,
 c. subjecting said at least one droplet to a direct detection, wherein the presence or relocalization of said detectable event within said at least one droplet determines the presence of said compound of interest.

A second aspect of the present invention relates to the use of the method according to the first aspect for monitoring a biological event.

A third aspect of the present invention is directed to a method for the detection of a compound of interest in a droplet comprising the steps of:
 a. providing a microfluidic system comprising:
  i. at least one inlet,
  ii. at least one outlet,
  iii. one or more channels,
 b. injecting in said microfluidic system a stream of droplets, wherein at least one droplet comprises:
  i. at least one single cell
  ii. a plurality of a first capturing agents capable of binding said at least one single cell as well as said compound of interest, and
  iii. a plurality of second capturing agents, each comprising a label, wherein said plurality of second capturing agents is capable of binding said compound of interest,
 c. incubating said droplets under conditions that allow the production of the compound of interest, whereby if the compound of interest is produced by the at least one single cell, it will be captured by said plurality of first and second capturing agents,
 d. determining the presence of the compound of interest by means of detecting a presence or relocalization of said label.

A fourth aspect of the present invention is directed to a microfluidic system comprising:
 a. at least one inlet,
 b. at least one outlet,
 c. one or more channels,
 d. a module for creating at least one droplet comprising:
  i. one or more single cell,
  ii. a first capturing agent,
  iii. a second capturing agent.
 e. a detection module detecting droplet containing cells producing a compound of interest
 f. an analysis module configured for the analysis of a signal.

A fifth aspect of the present invention relates to the use of a microfluidic system according to the fourth aspect for carrying out the method according to the first or third aspect.

DESCRIPTION OF THE FIGURES

FIG. 1. Single cell in-droplets secretion assay applied to cytokine secretion detection.

Figure 4A:
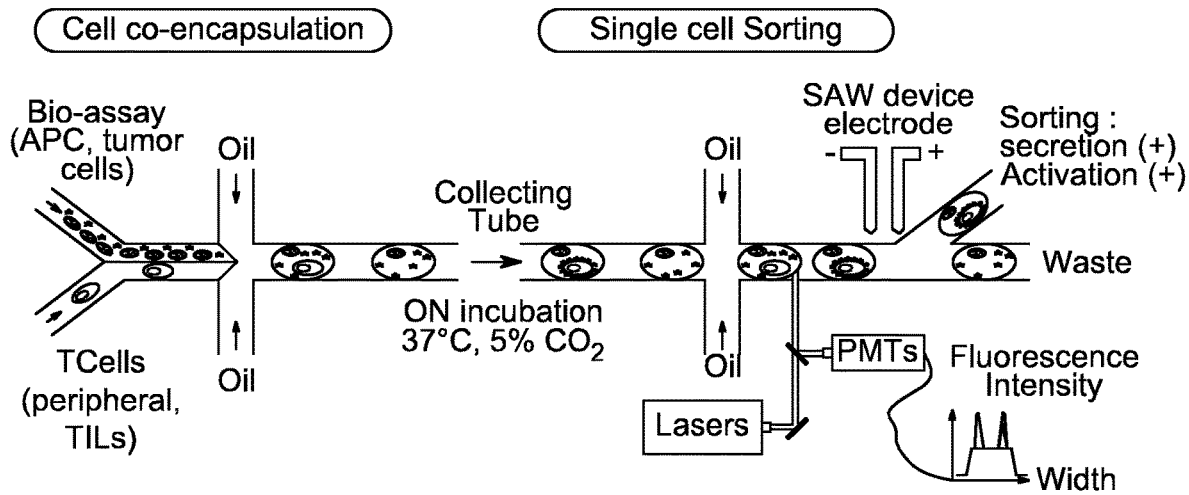

While the examples presented here are focusing on cytokine and/or antibody secretion detection using a fluorescent detection reagent, the presented assay can be applied to the secretion detection of any compound of interest and using any labelled detection reagent. PBMC are stimulated (either specifically using Antigen Presenting Cells labelled with specific Antigen or non-specifically, for example by the use of cross-linking antibodies or phorbol esters) either on-chip (i.e. in the droplet) or off-chip (i.e. out of the droplet, in a separate container) are pre-labeled (either on or off chip) with the capture reagent and encapsulated as single-cells into droplets together with the fluorescent detection reagent in conditions preventing cytokine secretion. After incubation of the droplets in conditions allowing cytokine secretion, the secreting cells are detected by the presence or relocalization of the detection reagent on the cell. A) Cytokine secreting cell: the cell is secreting the cytokine of interest, which binds to the capture reagent. The detection reagent binds to the secreted cytokine, thus leading to the presence or relocalization of the fluorescent signal on the cell. B) Non-secreting cells: the analyzed cell is not secreting the cytokine of interest and the detection reagent stays homogeneous in the droplet. No presence or relocalization of fluorescence is observed.

FIG. 2. Single cell in-droplets detection of IFNγ secretion is sensitive and specific.

A) Single cell droplet-based detection of secreted IFNγ specifically by activated T-cells, compared to non-activated. Cells that were dead before the experiment or died in the droplets before or after secreting the cytokine of interest are excluded from the analysis, by the addition in droplet of NucRed™ brand or NucGreen™ brand intercalating agent, to prevent any non-specific events, which can represent a substantial non-specific binder. In droplets, secretion of IFNγ is detected for 0.14% and 16.7% in droplet containing non-activated and activated cells, respectively. B) Flow based detection of IFNγ secretion by activated T-cells. In flow cytometry, secretion of IFNγ is detected for 0% and 16% of non-activated and activated cells respectively. The shift of cells population is a severe limitation of the flow-based system due to high background of non-specific capture of secreted molecules by cells nearby during staining.

FIG. 3. Single cell in-droplets detection of IFNγ secretion is sensitive (<1 nM), efficient (>80%) and 100% specific.

Droplets containing single non-activated CD8+ T-cells, pre-labelled with the capture reagent, and co-flowed with the detection reagent, in the presence of different concentrations of purified IFNγ were reinjected into the microfluidic device and fluorescence of each droplet was analyzed using proprietary software. A) Selection of droplets having the correct width and attribution of the different emulsions/concentration conditions. B) Selection of droplets containing CD8+ T-cells based on cell-labeling. C) Detection of IFNγ in droplets for each concentration of cytokine tested. D) For each concentration of IFNγ tested, the percentage of positive droplets detected was determined and compared to the negative control (0 nM). As low as 1 nM of cytokine was detectable in droplets and about 80% of the cells were detected using the droplet based single cell secretion assay. No false positive was selected as 0% of cells/droplet were observed as positive in the condition containing 0 nM IFNγ.

Figure 4B:
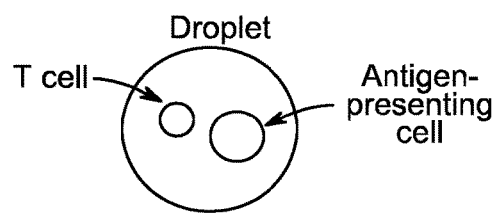
Figures 4C, 4D:
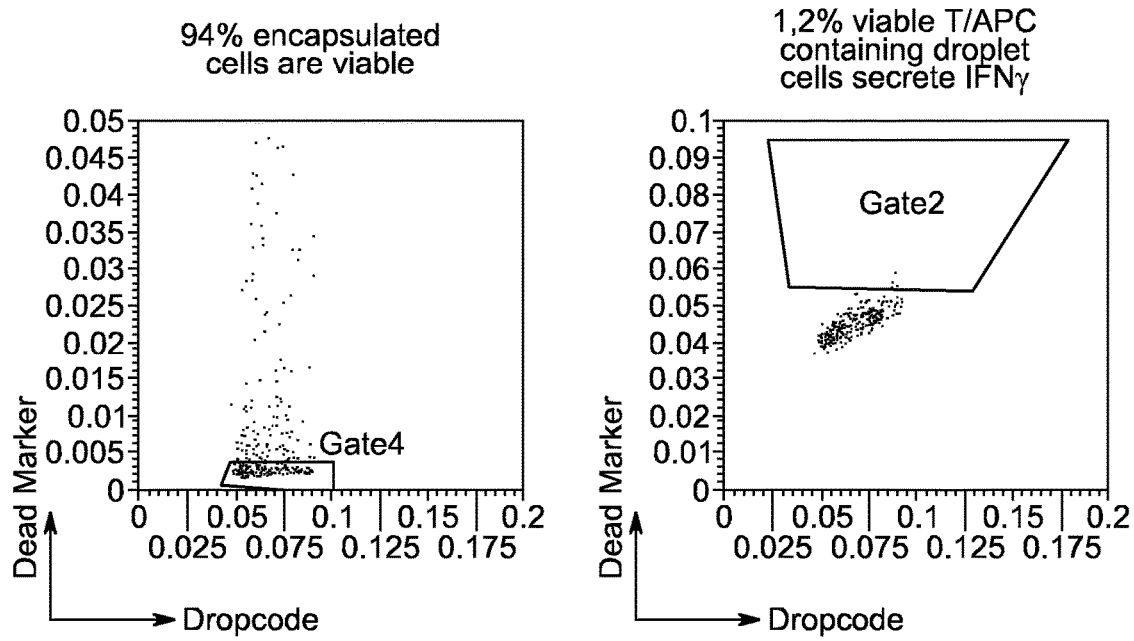

FIG. 4. Single cell in-droplet antigen-specific activation of T cells by antigen-presenting cell.

A) Antigen-presenting cells (APC) pulsed with a specific peptide pool and primary CD8+ T-cells (pre-labelled with capture reagent) were co-encapsulated in droplets. Droplets were incubated over-night in conditions allowing activation of T-cells by APC, which was detected by cytokine secretion. The following day, droplets were reinjected in the microfluidic device and fluorescence signals were analyzed for detection of activated T-cells having secreted and secreting IFNγ. B) Droplets of interest were composed of one T-cell and one antigen presenting cell co-encapsulated. Both cells can be fluorescently labeled in different colors to enable effective selection of droplets containing both cells. C) A fluorescent dead cell marker was used to control viability of cells in droplets and exclude any false positives due to cell death, either before or during the course of the experiment/activation. Cells encapsulated into droplets showed high viability after over-night incubation as 94% of them were detected as viable. D) The droplet secretion assay was used to detect antigen-specific T-cell activation by APC in droplets. As anticipated, based on responsive T-cell frequency, 1.2% of droplets containing both a viable T-cells and a viable APC were detected as secreting IFNγ indicating a successful, high viability, antigen-specific activation and detection of activated cells based on IFNγ secretion of single T-cells in droplets.

Figure 5A:
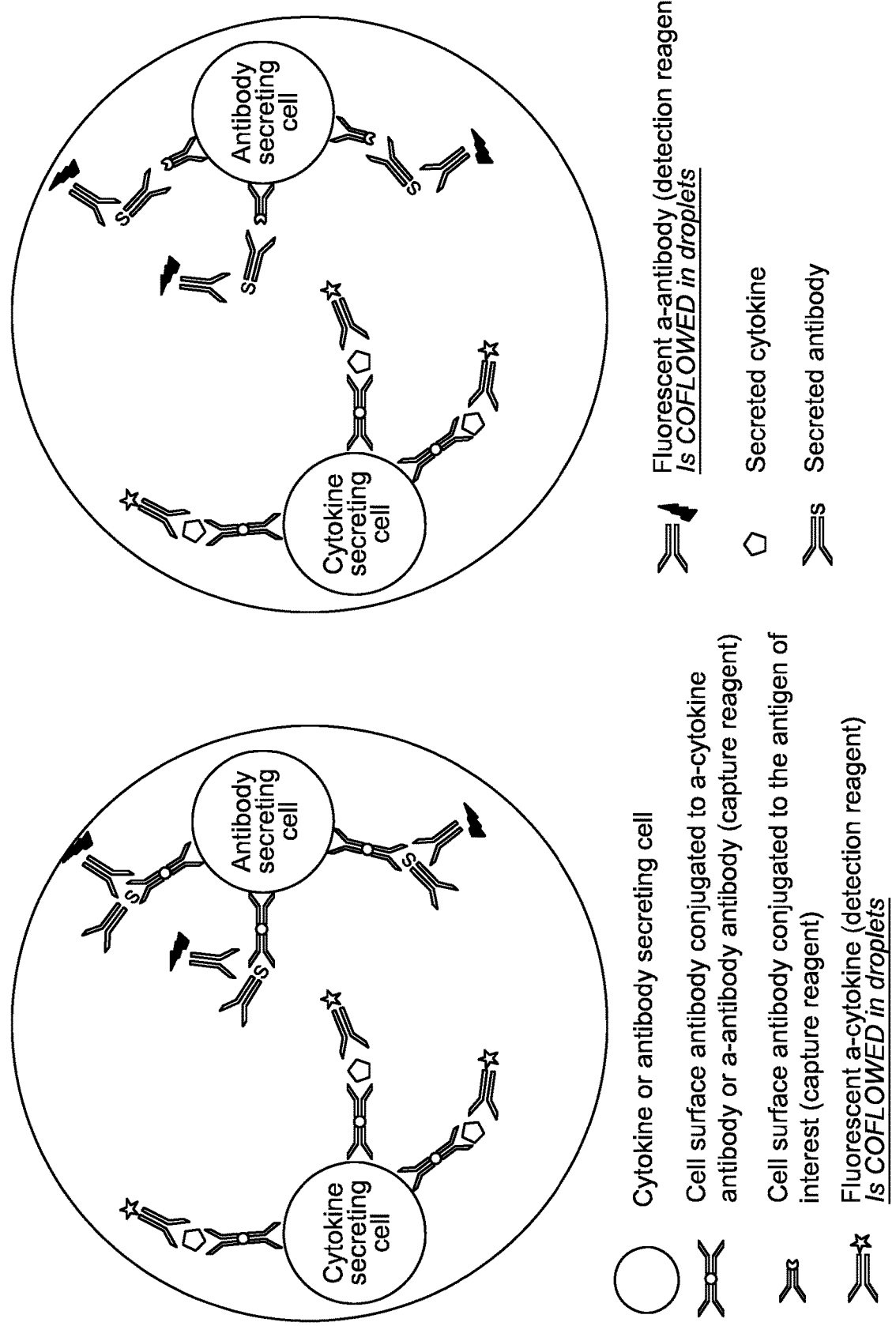

FIG. 5. Single cell in-droplet secretion assay applied to any secreted molecule detection.

The method according to the present invention is highly modulable and can be adapted to detect a variety of biological events. While the examples presented here are focusing on cytokine and/or antibody secretion detection using a fluorescent detection reagent, the presented assay can be applied to the secretion detection of any compound of interest and using any labelled detection reagent. (A) Example of in-droplet detection of the secretion of diverse compounds of interest by the interrogated cells, including the possibility for multiplexed assays. Here, multiplexed assay of antibody and cytokine secretion is presented but the present invention can be applied to any mentioned compound of interest. Off- or on-chip stimulated PBMC are pre-labeled with the cytokine specific capture reagent and B cells are prelabeled with the antibody specific capture reagent. Both cell populations are co-encapsulated as single-cells into droplets together with the cytokine-specific fluorescent detection reagent and the antibody-specific fluorescent detection reagent in conditions preventing cytokine and antibody secretion before they are encapsulated as individual cells. The labels (fluorescent in this example but can be by any means) of both detection reagents are selected wisely according to the assay. After incubation of the droplets in conditions allowing cytokine and antibody secretion, the secreting cells are detected by the presence or relocalization of the detection reagents on the cells. The secreted cytokine is bound to the capture reagent specifically bound to the cytokine-secreting cells and detected through the presence or relocalization of the fluorescent anti-cytokine detection reagent. The secreted antibody is bound to the capture reagent bound to the antibody-secreting cell and detected through the presence or relocalization of the fluorescent anti-antibody detection reagent on the cell. The antibody-specific capture reagent can be specific for all immunoglobulins allowing global antibody response to be detected or composed of the antigen of interest allowing antigen-specific antibody response to be detected. (B) Example of in-droplet cytokine secretion detection with coflowed capture and detection reagents. Off- or on-chip stimulated PBMC are encapsulated as single-cells into droplets together with the capture reagent and detection reagent (can be fluorescent as exemplified here or can be any other mean) in conditions preventing cytokine secretion. After incubation of the droplets in conditions allowing cytokine secretion, the secreting cells are detected by the presence or relocalization of the detection reagents on the cells. Both capture and detection reagent concentrations are adapted to generate the highest signal/background ratio and enabling the maximal fluorescent signal onto the interrogated cell. (C) Example of in-droplet cytokine secretion detection with the first capture reagent bound to the cells being composed of two or more molecules. Off- or on-chip stimulated PBMC are pre-labeled with the cytokine specific capture reagent composed of two or more molecules. The two or more molecules are composed of an antibody specific to the cell membrane of interest conjugated to a ligand A and an antibody specific to the cytokine of interest conjugated to a ligand B; where ligands A and B can interact and form a stable association. The cells are encapsulated as single-cells into droplets together with the fluorescent detection reagent in conditions preventing cytokine secretion. After incubation of the droplets in conditions allowing cytokine secretion, the secreting cells are detected by the presence or relocalization of the detection reagent on the cells. (D) Example of in-droplet cytokine secretion detection with the first capture reagent being coflowed and composed of two or more molecules. Off- or on-chip stimulated PBMC are encapsulated as single-cells into droplets together with the capture reagent and fluorescent detection reagent in conditions preventing cytokine secretion. The coflowed cytokine specific capture reagent is composed of two or more molecules. The two or more molecules are composed of an antibody specific to the cell membrane of interest conjugated to a ligand A and an antibody specific to the cytokine of interest conjugated to a ligand B; where ligands A and B can interact and form a stable association. After incubation of the droplets in conditions allowing cytokine secretion, the secreting cells are detected by the presence or relocalization of the detection reagent on the cells. Both capture and detection reagent concentrations are adapted to generate the highest signal/background ratio and enabling the maximal fluorescent signal onto the interrogated cell. (E) Example of in-droplet cytokine secretion detection with the first capture reagent being composed of two molecules, one moiety being bound to the cell, the other being coflowed. Off- or on-chip stimulated PBMC are pre-labeled with the first moiety of the capture reagent composed an antibody specific of the cell membrane conjugated to a ligand A. The cells are encapsulated as single-cells into droplets together with the second moiety of the capture reagent composed of an antibody specific to the cytokine of interest conjugated to a ligand B as well as with the fluorescent detection reagent in conditions preventing cytokine secretion. Ligands A and B can interact and form a stable association. After incubation of the droplets in conditions allowing cytokine secretion, the secreting cells are detected by the presence or relocalization of the detection reagent on the cells. Both the second moiety of the capture reagent and the detection reagent concentrations are adapted to generate the highest signal/background ratio and enabling the maximal fluorescent signal onto the interrogated cell.

FIG. 6. Detection of T cell activation by secreted receptor-specific antibody.

FIG. 7. Double positive detection of ADCC induced by secretion of antigen-specific antibody and cytotoxic factors secretion detection.

Figure 8:
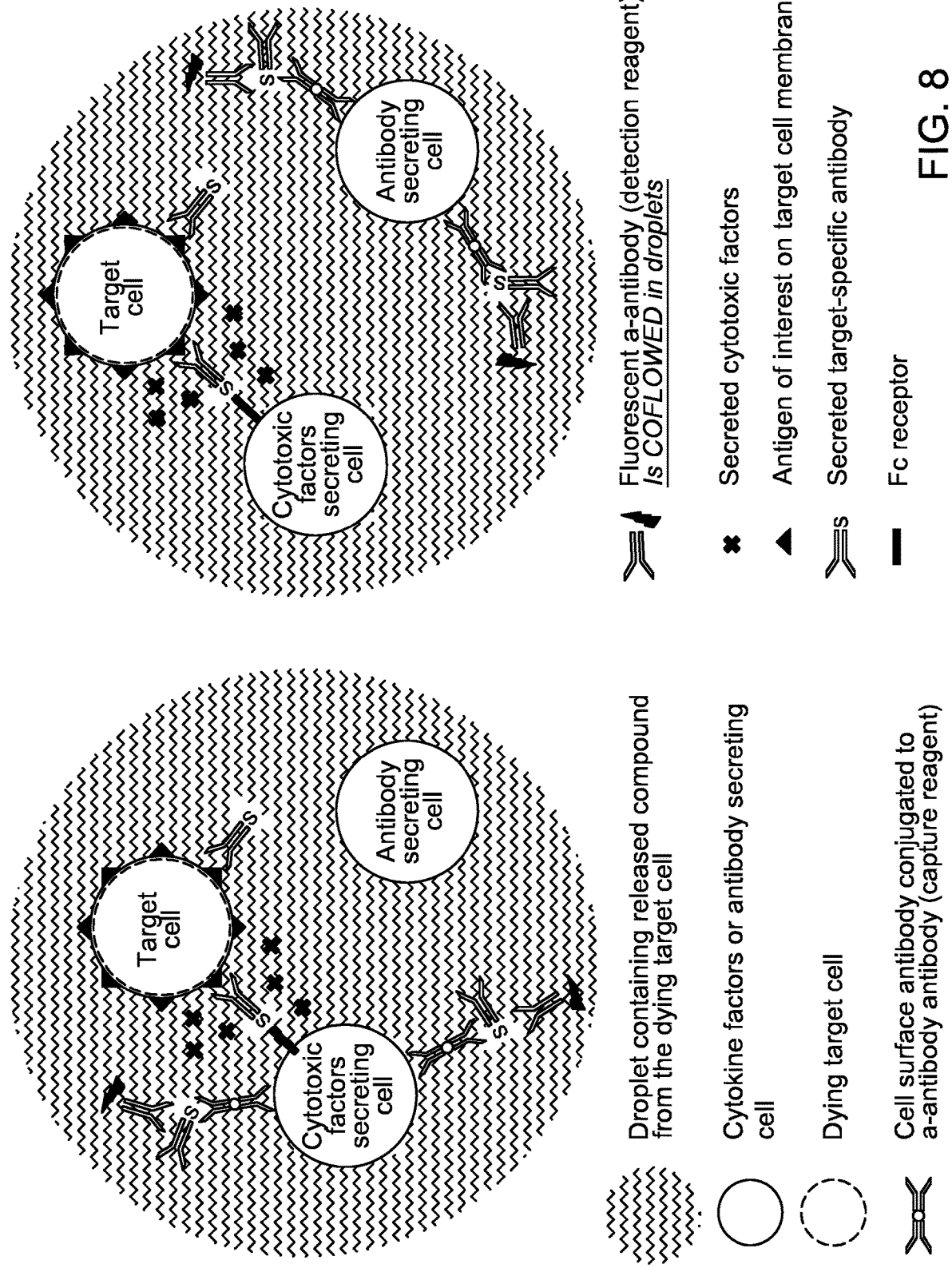

FIG. 8. Double positive detection of ADCC induced by secretion of antigen-specific antibody.

Figure 9:
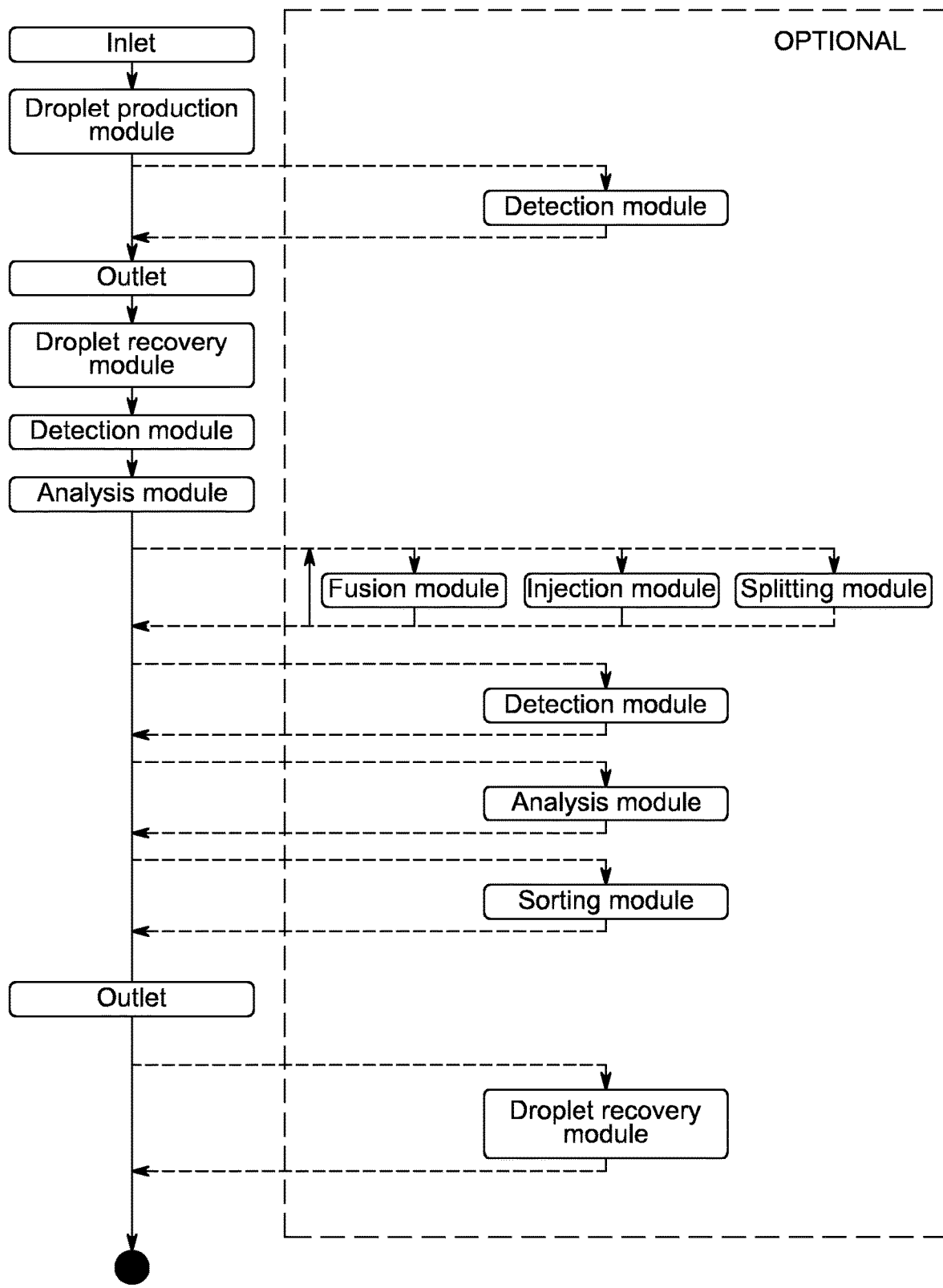

FIG. 9. Description of the microfluidic system and process according to the invention.

DETAILED DESCRIPTION OF THE INVENTION

The method according to the present invention is intended to solve the above-mentioned issues affecting current microfluidic techniques for single cell analysis. In particular, the present method provides an improved performance in detecting, analyzing and/or quantifying the production of a compound of interest at single cell level.

A first advantage of the method disclosed herein is represented by its high sensitivity. Such property is due to the spatial confinement of a single cell producing a compound of interest in a droplet, wherein said single cell has freedom of mobility, allowing high viability and thus high, yet physiological, metabolic activity. In addition, the spatial confinement of a single cell producing a compound of interest in a droplet, wherein said secreted product is confined in a constrained few pico to nano-liter volume allows reaching high concentration in few minutes to hours of incubation, depending on the produced molecule.

Consequently, a second advantage emerging by using the method of the present invention is represented by the possibility of carrying out kinetic analysis by virtue of monitoring a change in the relocalization and/or intensity of a detectable event in real-time. By extension, it is easy to envision extending to multiple secreted compound detection, by using differently labelled detection reagent.

Consequently, a third advantage emerging by using the method of the present invention is represented by the possibility of carrying out complex, yet flexible sets of assays by virtue of co-encapsulating two or more cells into the droplets and monitoring the role of cell-cell interaction for production of said compound by one, two or more cells. Those complex assays co-encapsulating two or more cells also enable the detection of the secretion of two or more compounds of interest.

A fourth advantage emerging by using the method of the present invention is represented by the high specificity of the detection of production of said molecule. Such property is due to the spatial confinement of a single cell producing a compound of interest in a droplet, wherein said secreted product is confined in a restrained volume, specifically captured to said single cells and secreted product is thus captured only by the secreting cells.

In this regard, the inventors have found that secreting cells are advantageously detected by monitoring the presence or relocalization of the detection reagents on the cell within the droplet and that cell density/concentration is not impacting the specificity of detection.

In addition, in case of the presence of a non-secreting cell or cell not secreting the compound of interest, the detection reagents remain homogeneous in the droplet, thus minimizing the false positive hit rate.

In a first aspect, the present invention relates to a method for the detection of a compound of interest in a microfluidic system, said method comprising the steps of:
 a. creating at least one droplet in said microfluidic system, said at least one droplet comprising:
  i. at least one single cell,
  ii. one or more first capturing agent, wherein said one or more first capturing agent is capable of binding said at least one single cell as well as said compound of interest,
  iii. one or more second capturing agent comprising a label, wherein said one or more second capturing agent is capable of binding said compound of interest,
 b. incubating said at least one droplet capable of generating a detectable event,
 c. subjecting said at least one droplet to a direct detection, wherein the presence or relocalization of said detectable event within said at least one droplet determines the presence of said compound of interest.

In the context of the present invention, the term "microfluidic system" may refer to one or more integrated units or chips for performing the method disclosed herein. Said microfluidic system is generally represented in the form of a microfluidic chip comprising one or more micro-channels and one or more microfluidic devices (e.g. micropumps, microvalves).

In the context of the present invention, a "microfluidic chip" generally refers to a set of micro-channels made by milling, etching, ablation or molding into a material (polymeric material such as polydimethylsiloxane (PDMS) or polymethylmethacrylate (PMMA), polycarbonate (PC), epoxy, cyclic olefin copolymer (COC) in particular photopolymerizable epoxy such as marketed by Norland Optical Adhesives (NOA), glass, silicon, plastics). A microfluidic chip may comprise a substrate and a support, defining together at least one channel.

As used herein, the term "droplet" refers to an isolated portion of a fluid which is immiscible with its surrounding. In the context of the present invention, said "droplet" may be spherical, substantially spherical or non-spherical in shape. Said shape may depend by different parameters, such as, for example, the external environment.

Methods for preparing, generating and injecting droplets in a microfluidic system are known to the person skilled in the art. An exemplary method is disclosed in US 2015/0057163 A1. With reference to the presence of a single cell in each droplet, the person skilled in the art is aware that this parameter can be controlled and/or estimated using the Poisson distribution.

In the context of the present invention, the expression "at least one single cell" refers to viable and non-viable single cell. The viability status of said at least one single viable cell can be altered or changed along the steps of the method according to the present invention. It is worth noting that, after the incubation step of a droplet according to the present method, the capability of generating a detectable event in said droplet refers to the possibility within the droplet of having at least one viable single cell.

As used herein, the term "direct detection" refers to the possibility of detecting the compound of interest produced by a single cell in absence of a solid support within the droplet, wherein the solid support would be used for capturing the compound of interest. In the context of the present invention, the terms "solid support" refers to any non-biological matrix, e.g. magnetic beads, gel matrix or affinity matrix, that has a given specificity for a target molecule such that the target molecule can be immobilized on said support, which allows isolation of the target molecule from the content comprised in the droplet.

According to an embodiment of the first aspect of the present invention, the single cell presents a freedom of mobility within the droplet.

In the context of the present invention, the detection of the compound of interest is independent from the orientation of the cell producing said compound of interest within the droplet.

According to another embodiment of the first aspect of the present invention, the single cell is not captured on a solid support.

The inventors have found that the presence of a single cell with a high degree of mobility, that is not constrained on a solid support allow a superior sensitivity in detecting the presence of a compound of interest secreted by the cell because of an improved distribution of first capturing agents on the cellular surface.

As used herein, the term "capturing agent" refers to a reagent, nucleic acid, protein or peptide that presents an affinity towards the compound of interest. In the context of the present invention, the method requires the presence of a first and a second capturing agent.

In the context of the present invention, the terms "first capturing agent" and/or "second capturing agent" may refer to a single bifunctional compound or to a complex comprising two or more different compounds, each characterized by a specific functionality. Examples of first and second capturing agents conceived for the method according to the present invention can be a compound or a complex formed of antibodies, antigens, cytokines, chemokines, hormones or growth factors or a combination of those.

As used herein, the term "relocalization" refers to a change in the spatial disposition within a droplet of density and/or concentration of a detectable event. As used herein, the term "presence" refers to the occurrence or change of the intensity of a detectable event.

An important aspect of the method according to the present invention relates to the relocalization of a detectable event within the droplet. In this regard, methods known in the art cannot achieve "relocalization" as intended herein, but only a local concentration-binding as the excess is washed away before doing the flow cytometry analysis. Therefore, the effect of this feature confers to the method according to the present invention a higher efficiency over the current methods.

Another important step in droplet-based microfluidic assays, along with droplet creation, pico-injection, merging and sorting, is represented by the incubation of droplets. In the context of the present invention, the incubation may occur off- or on-chip. The incubation step may also occur in a delay line necessary for incubating droplets for a precise time allowing for cells viability and production of a compound of interest. An exemplary method of incubation in delay lines is disclosed in US 2012/0121480 A1. Typical incubation temperature before encapsulation ranges from 0° C. to 16° C., after encapsulation ranges from 16° C. to 38° C., and re-injection for analysis of secreted molecule after incubation ranges from 0° C. to 38° C. Typical incubation time goes from milliseconds (for kinetics analysis) to more than 24 h (for cell-cell interaction mediated compound production regulation analysis).

In another embodiment of the first aspect of the present invention, the method further comprises the step of measuring cell viability in droplets after incubation. In the context of the present invention, a preferred method for measuring cell viability is carried out by using an intercalating dye that emits fluorescence only if a dead cell is detected in the droplet, e.g. NucRed™ Dead 647 ReadyProbes™ brand dye.

According to another embodiment of the first aspect of the present invention, the one or more first capturing agent binds the surface of said at least one single cell before or after creating said at least one single droplet.

In one embodiment of the first aspect of the present invention, the one or more first capturing agent binds said single cell with a density ranging from $10^1$ to $10^8$ molecules/cell.

According to another embodiment of the first aspect of the present invention, the compound of interest is produced in the droplet with a concentration of 10 pM to 100 μM.

In another embodiment of the first aspect of the present invention, the droplet has a volume ranging from 2 pL to 10 nL.

In another embodiment of the first aspect of the present invention, the label is selected from the group comprising a fluorescent label, a polymer, a protein, a peptide, a hapten, a chemical, a nucleic acid or a barcode label. As used herein, the term "barcode" refers to a label that may be attached to an analyte to convey information about said analyte. In the context of the present invention, the barcode label can be a mixture of labels, polymer, fluorescent label, peptide, hapten, protein, chemicals, nucleic acid.

In another embodiment of the first aspect of the present invention, the first capturing agent and said second capturing agent are independently selected from the group comprising a protein, a peptide, an oligonucleotide, a hapten, a nucleic acid, a fluorescent conjugate, an enzyme conjugate, a synthetic polymer or a barcode or a combination thereof. The barcode label can be a mixture of labels, said polymer, fluorescent label, peptide, haptene, protein, chemicals, nucleic acid.

In another embodiment of the first aspect of the present invention, the first capturing agent is an antibody and said second capturing agent is a fluorescent anti-compound of interest antibody.

According to another embodiment of the first aspect of the present invention, the first capturing agent is a bifunctional antibody.

In another embodiment of the first aspect of the present invention, the compound of interest is a cell-secreted compound selected from the group including but not limited to antibody (IgG (IgG1, IgG2, IgG3, IgG4), IgE, IgA (IgA1, IgA2), IgM), cytokine (IL-1-like, IL-1α, IL-1β, IL-1RA, IL-2, IL-3, IL-4, IL-5, IL-6-like, IL-6, IL-7, IL-9, IL-10-like, IL-10, IL-11, IL-12, IL-13, IL-14, IL-15, IL-16, IL-17, IL-18, IL-20, Common b chain (CD131), LIF, OSM, Interferons (IFN-α, IFN-β, IFN-γ), TNF, TNF-α, TNF-β, CD153, CD154, LT-β, 4-1BBL, APRIL, CD70, CD132, CD178, GITRL, LIGHT, OX40L, TALL-1, TRAIL, TWEAK, TRANCE, TGF-β, Tpo, Flt-3L, SCF, M-CSF, MSP), chemokine (CCL1, CCL2, CCL3, CCL4, CCL5, CCL6, CCL7, CCL8, CCL9/CCL10, CCL11, CCL12, CCL13, CCL14, CCL15, CCL16, CCL17, CCL18, CCL19, CCL20, CCL21, CCL22, CCL23, CCL24, CCL25, CCL26, CCL27, CCL28, CXCL1, CXCL2, CXCL3, CXCL4, CXCL5, CXCL6, CXCL7, CXCL8, CXCL9, CXCL10, CXCL11, CXCL12, CXCL13, CXCL14, CXCL15, CXCL16, CXCL17, XCL1, XCL2, CX3CL1), hormones (estrogene, progestogens, thyroxine, steroids, insulin, adrenaline Epinephrine, Melatonin, Triiodothyronine, Thyroxine, Prostaglandins, Leukotrienes, Prostacyclin, Therocis, Adiponectin, Adrenocorticotropic hormone (or corticotropin), Amylin (or Islet Amyloid Polypeptide), Angiotensinogen and angiotensin, Anti-Müllerian hormone (or Müllerian inhibiting factor or hormone), Antidiuretic hormone (or vasopressin, arginine vasopressin), Atrial-natriuretic peptide (or atriopeptin), Calcitonin, Cholecystokinin, Corticotropin-releasing hormone, Cortistatin, Endothelin, Enkephalin, Erythropoietin, Follicle-stimulating hormone, Galanin, Gastric inhibitory polypeptide, Gastrin, Glucagon, Glucagon-like peptide-1, Gonadotropin-releasing hormone, Guanylin, Hepcidin, Human chorionic gonadotropin, Inhibin, Insulin, Insulin-like growth factor (or somatomedin), Leptin, Lipotropin, Melanocyte stimulating hormone, Motilin, Orexin, Osteocalcin, Oxytocin, Relaxin, Renin, Secretin, Somatostatin, Thrombopoietin, Uroguanylin, Vasoactive intestinal peptide, Steroid, estrogen, glucocorticoid, progestogen, secosteroid), growth factors (G-CSF, GM-CSF, Fas-ligand, Adrenomedullin (AM), Angiopoietin (Ang), Autocrine motility factor, Bone morphogenetic proteins (BMPs), Ciliary neurotrophic factor family, Ciliary neurotrophic factor (CNTF), Leukemia inhibitory factor (LIF), Interleukin-6 (IL-6), Colony-stimulating factors, Macrophage colony-stimulating factor (m-CSF), Granulocyte colony-stimulating factor (G-CSF), Granulocyte macrophage colony-stimulating factor (GM-CSF), Epidermal growth factor (EGF), Ephrins (A1-A5, B1-B3), Erythropoietin (EPO), Fibroblast growth factor (FGF1-FGF23), Foetal Bovine Somatotrophin (FBS), GDNF family of ligands, Glial cell line-derived neurotrophic factor (GDNF), Neurturin, Persephin, Artemin, Growth differentiation factor-9 (GDF9), Hepatocyte growth factor (HGF), Hepatoma-derived growth factor (HDGF), Insulin, Insulin-like growth factors, Insulin-like growth factor-1 (IGF-1 and IGF-2), Interleukins; IL-1—Cofactor for IL-3 and IL-6, IL-2, IL-3, IL-4, IL-5, IL-6, IL-7, Keratinocyte growth factor (KGF), Migration-stimulating factor (MSF), Macrophage-stimulating protein (MSP), also known as hepatocyte growth factor-like protein (HGFLP), Myostatin (GDF-8), Neuregulins (NRG1-NRG4), Neurotrophins, Brain-derived neurotrophic factor (BDNF), Nerve growth factor (NGF), Neurotrophin-3 (NT-3), Neurotrophin-4 (NT-4), Placental growth factor (PGF), Platelet-derived growth factor (PDGF), Renalase (RNLS)—Anti-apoptotic survival factor, T-cell growth factor (TCGF), Thrombopoietin (TPO), Transforming growth factor alpha (TGF-α, TGF-β (TGF-β1, TGF-β2, TGF-β), Tumor necrosis factor-alpha (TNF-α), Vascular endothelial growth factor (VEGF)).

A second aspect of the present invention encompasses the use of the method according to the first aspect of said invention for monitoring one or several, potentially simultaneous, biological event(s). As used herein, the term "biological event" refers to describe an alteration of a physiological process and/or state occurring in a subject's body and affecting the physiological status of living cells. Typical example is linking secretion of a compound with induced mortality (ADCC, CDC, ADCP, Cytokine induced Cytolysis, Apoptosis, Chromium Release, as non-limiting examples), another example is activation and/or inhibition of cellular pathway by secreted compound (G protein coupled receptor activation, B-arrestin, caspase activation, PKC/NFKB pathways, MAP kinases, Pi3K, AKT pathway, Ras/Mek/Erk, PLC/$Ca^{++}$, as non-limiting examples).

In an embodiment of the second aspect of the present invention, the biological event is an immune response. Typical examples are detection of antigen recognition by T cells inducing compound secretion, including antigen recognition by B cells inducing compound secretion, including as well T cell activation monitored by secreted compound from T cells and induced by a second secreted compound (this example include detection of secreted compound by two different cell types and differentiating these using barcode specific for each one), and include B cell activation monitored by secreted compound from B cells and induced by a second secreted compound.

In a third aspect of the present invention, there is provided a method for the detection of a compound of interest in a droplet comprising the steps of:
  a. providing a microfluidic system comprising:
    i. at least one inlet,
    ii. at least one outlet,
    iii. one or more channels,
  b. injecting in said microfluidic system a stream of droplets, wherein at least one droplet comprises:
    i. at least one single cell
    ii. a plurality of a first capturing agents capable of binding said at least one single cell as well as said compound of interest, and
    iii. a plurality of second capturing agents, each comprising a label, wherein said plurality of second capturing agents is capable of binding said compound of interest,
  c. incubating said droplets under conditions that allow the production of the compound of interest, whereby if the compound of interest is produced by the at least one single cell, it will be captured by said plurality of first and second capturing agents,
  d. determining the presence of the compound of interest by means of detecting a presence or relocalization of said label.

A fourth aspect of the present invention relates to a microfluidic system comprising:
  a. at least one inlet,
  b. at least one outlet,
  c. one or more channels,
  d. a module for creating at least one droplet comprising:
    i. one or more single cell,
    ii. a first capturing agent,
    iii. a second capturing agent,
  e. a detection module detecting droplet containing cells producing a compound of interest.
  f. an analysis module configured for the analysis of a signal.

According to an embodiment of the fourth aspect of the present invention, the microfluidic system is characterized by the presence of at least two modules in communication with each other selected from the group comprising: module for droplet production, module for droplet detection, module for droplet analysis, module for sorting droplets, module for tagging droplets and module for recovering droplets. In the context of the present invention, the module for recovering droplets is intended for carrying out additional process (e.g. genotyping, further functional analysis).

An ideal scheme of the microfluidic system and process according to the present invention is depicted in FIG. 9.

The combination of two or more of the aforementioned modules allows the microfluidic system disclosed herein to achieve improved results in terms of high-throughputability (several thousand of droplets per second can be processed).

An important aspect of the microfluidic system according to the present invention is that secretion and detection steps according to the method of the first aspect of the present invention can be performed in the same module of the microfluidic system.

According to a fifth aspect, the microfluidic system according to the fourth aspect is used for carrying out the method disclosed in the first or third aspect of the present invention.

Examples

Principle Description

Healthy donor human PBMC are pre-labeled in microtubes with an excess of a bi-functional antibody, called "catch reagent". The catch reagent is specific for both a leucocyte-specific membrane protein (CD45) and the cytokine of interest. After 5 minutes incubation in conditions preventing cytokine secretion (i.e. at 4° C.), all the leucocytes are evenly labeled with the catch reagent and the excess is washed away by extensive washes. Pre-labeled cells are encapsulated as single-cells into picoliter droplets with 1% v/v final concentration of fluorescently-labeled anti-cytokine antibody in conditions preventing cytokine secretion (FIG. 1). The droplets containing single-cells are incubated for 1 h20 at 37° C. in a 5% $CO_2$-controlled incubator to enable cytokine secretion. Droplets are reinjected and the secretion of cytokine, traduced by the relocalization of the detection reagent's fluorescent signal on the cell is analyzed for each droplet. In a droplet containing a cytokine-secreting cell, the detection reagent signal is relocalized onto the cell, leading to a local increase of fluorescence in the droplet. On the contrary, in a droplet containing a non-secreting cell, the detection reagent's fluorescent signal stays homogeneous in the droplet and no local increase of fluorescence is observed.

Applications

Cytokine Secretion Detection

In-droplet secretion assay was applied to the detection of IFNγ (and TNFα, not shown) secretion by PMA/ionomycin activated PBMC compared to non-activated PBMC (FIG. 1). The results observed using droplet based microfluidic system and software were compared to flow cytometry data generated in microplates with the same cells and conditions (FIG. 2). 100% of secreting cells in flow cytometry were detected as positive in the droplet secretion assay. False positive cells counted for less than 0.15% in the negative control. The droplet detection of cytokine secretion by activated T cell is highly efficient and specific compared to flow cytometry detection.

Quantification of Cytokine Secretion Sensitivity and Efficiency

Non-activated and non-secreting CD8+ T-cells were encapsulated in droplets with a range of concentration of purified IFNγ following the droplet secretion assay procedure. Four emulsions were produced, each containing cells isolated as single cells and purified cytokine at different concentrations: 0 nM, 1 nM, 5 nM or 10 nM final concentration of IFNγ in droplets (FIG. 3). Droplets of all four emulsions were reinjected and fluorescence signals were analyzed. Using the droplet secretion assay, as low as 1 nM cytokine concentration was detected with no false positive events showing a highly sensitive and 100% specific assay. The secreting assay also showed to be efficient as more than 80% of the positive cells were detected in droplets.

These examples show the possibility to calibrate assay detection for quantitative, real-time cytokine secretion quantification in droplet by the mean of generating standard curve samples conditions.

Antigen Specific T Cells Identification Based on Cytokine Secretion from Co-Encapsulated APC/T-Cells in Droplet When co-cultured, antigen-presenting cells (APC) loaded with a specific peptide can specifically activate a subset of responding T-cells, leading to cytokine secretion. The droplet secretion assay was applied to detection of specific activation of T-cells by APC in droplets (FIG. 4). APC and T-cells were co-flowed as single-cells into droplets in conditions preventing cytokine secretion. Droplets were incubated over-night at 37° C. in 5% $CO_2$ controlled incubator and reinjected the following day. Viability of both T-cells and APC was measured after over-night incubation in droplets, by using the NucRed™ brand intercalating dye. Using such dead cell fluorescent marker, 94% of the encapsulated cells were detected as viable. Specific activation of T-cell by APC was detected using the droplet secretion assay applied to IFNγ secretion. Within droplets containing viable T-cells and APC, 1.2% secreted IFNγ, demonstrating effective antigen-specific activation of T-cells in droplets.

Antigen-Specific and Total Antibody Secretion Detection

Antibody secretion can be assessed using the presented in-droplet secretion assay by co-encapsulating in droplets B cells prelabeled with the capture reagent together with the detection reagent. The capture reagent's first moiety is capable of recognizing a B cell surface marker, can be a Pan-B marker or a specific B cells marker, typical example is the CD138 marker for immunoglobulin secreting plasma cells. The second moiety of the capture reagent either specifically captures antibody or consists of the antigen of interest. In the first case where the capture reagent is composed of a moiety capturing antibody, the detection reagent is composed of a detectable labeled antigen. In the second case where the capture reagent is composed of the antigen of interest, the detection reagent is composed of a detectable labeled anti-antibody secondary. The relocalization of the fluorescent signal on the B cell (labels are here fluorescent but can be detected by any means for people skilled in the art) indicates antigen specific antibody secretion by the B cell present in the interrogated droplet. The method described here can be adapted with or without pre-incubation of the capture reagent (FIGS. 5A-E). The method described here can be adapted to any compound of interest previously mentioned.

Detection of T Cell Activation by Secreted Receptor-Specific Antibody

Binding of antibodies specific to a given T cell receptor can activate the T cell leading to, for example, cytokine secretion. The droplet secretion assay can detect T cell activation by a T cell receptor-specific antibody secreted by an immunoglobulin expressing cell in the droplet (FIG. 6). Typical example includes PBMC prelabelled with the capture reagent encapsulated into droplets together with an immunoglobulin expressing cell. The droplets are produced while containing the labeled detection reagent (labels are here fluorescent but can be by any means) and in conditions preventing antibody production. After incubation of the droplets in conditions allowing antibody production, T cell activation is detected through detection of, for example, cytokine secretion. Binding of the T cell receptor-specific antibody activates in turn the T cell which then secretes, for example, cytokines. The secreted cytokines relocalize onto the capture reagent bound to the T cell and the fluorescent detection reagent relocalizes onto the cytokine of interest. Droplets containing a T cell activated by a secreted antibody present then a detectable signal due to the relocalization of the detection reagent on the activated T cell. The method described here can be adapted with or without pre-incubation of the capture reagent. Typical examples of the method described above is the detection of anti-CD3 antibodies triggering the T cell activation. By extension, the system can be used for the identification of anti-checkpoints antibodies.

Double Positive Detection of ADCC Induced by Secretion of Antigen-Specific Antibody and Cytotoxic Factors Secretion Detection The in-droplet secretion assay can be used to assess induced mortality in case of an antigen-specific antibody having ADCC activity is secreted (FIG. 7). The double positive assay presented here enables the detection of both the cytotoxic factors secretion by the killing cells (example include primary natural killer (NK) cells, monocytes, macrophages, neutrophils, eosinophils and dendritic cells, as well as cell culture cell lines) and death of the target cell induced by the compound secreted by the killing cell. Killing cells are pre-labeled with the catch reagent specific to the cytotoxic factors of interest in non-saturating conditions. Non-saturating conditions of capture reagent are mandatory to enable both capture and detection of secreted compound of interest secretion by killing cell and effect of the secreted compound, yet not captured, on the target cell ultimately inducing cell death. The target cell is then co-encapsulated in droplet with an immunoglobulin producing cell and a killing cell. The encapsulated cells are coflowed with the detection reagent specific to the cytotoxic factors of interest in conditions preventing antibody production before encapsulation. After production, the droplets are incubated in conditions allowing antibody production. The specific antibody relocalizes on the target cell and the killing cell binds the antibody through the Fc receptors. Once bound to the antibody having ADCC activity, the killing cell releases cytotoxic factors causing the death of the target cell. Some of the secreted cytotoxic factors are captured by the capture reagent on the killing cell and relocalize the detection reagent, enabling detection of the cytotoxic factors production. Cell death is monitored by the release of a compound from the dying target cell expressing the antigen of interest. Alternatively, cell death is monitored by cell surface marker, or any other suitable marker known by people skilled in the art. By extension, the in-droplet assay could be applied to Complement Dependent Cytotoxicity and Opsonophagocytosis or any other assays described above.

Alternative and/or complementary to this example is where the production of the antibody is detected in place (and/or in addition to) of the secreted cytotoxic factor, in combination or without the cell death detection (FIG. 8).

The invention claimed is:
1. A method for the detection of a compound of interest in a microfluidic system, said method comprising:
 a. creating, in said microfluidic system, at least one droplet capable of generating a detectable event, said at least one droplet comprising:
  i. at least one single cell;
  ii. one or more first capturing agent, wherein said one or more first capturing agent is capable of binding said at least one single cell as well as said compound of interest; and
  iii. one or more second capturing agent comprising a label, wherein said one or more second capturing agent is capable of binding said compound of interest;
 b. incubating said at least one droplet; and
 c. subjecting said at least one droplet to a direct detection; wherein the presence or relocalization of said detectable event within said at least one droplet is indicative of the presence of said compound of interest, wherein the compound of interest is produced by said at least one single cell, and wherein said at least one or more first capturing agent is bound to said at least one single cell before said at least one droplet is formed.

2. The method according to claim 1, wherein said one or more first capturing agent binds said at least one single cell with a density ranging from $10^1$ to $10^8$ molecules/cell.

3. The method according to claim 1, wherein said compound of interest is produced in said at least one droplet with a concentration of 10 pM to 100 μM.

4. The method according to claim 1, wherein said at least one droplet has a volume ranging from 2 pL to 10 nL.

5. The method according to claim 1, wherein said method further comprises measuring cell viability in said at least one droplet after incubation.

6. The method according to claim 1, wherein said label is a fluorescent label, an amino-acid based label, a nucleic acid based label, or a barcode label.

7. The method according to claim 1, wherein said one or more first capturing agent and said one or more second capturing agent are independently a protein, a peptide, an oligonucleotide, a nucleic acid, a fluorescent conjugate, an enzyme conjugate, a synthetic polymer, or a combination thereof.

8. The method according to claim 7, wherein said one or more first capturing agent is an antibody, and said one or more second capturing agent is a fluorescent anti-compound of interest antibody.

9. The method according to claim 8, wherein said one or more first capturing agent is a bifunctional antibody.

10. The method of claim 1, wherein said compound of interest is a cell-secreted compound, and is
 (i) antibody (IgG1, (IgG2, IgG3 or IgG4), IgE, IgA (IgA1 or IgA2), IgM);
 (ii) cytokine (IL-1-like, IL-1α, IL-1β, IL-1RA, IL-2, IL-3, IL-4, IL-5, IL-6-like, IL-6, IL-7, IL-9, IL-10-like, IL-10, IL-11, IL-12, IL-13, IL-14, IL-15, IL-16, IL-17, IL-18 or IL-20),
 (iii) Common b chain (CD131), LIF, OSM;
 (iv) Interferon (IFN-α, IFN-β or IFN-γ), TNF, TNF-α, TNF-β, CD153, CD154, LT-β, 4-1BBL, APRIL, CD70, CD132, CD178, GITRL, LIGHT, OX40L, TALL-1, TRAIL, TWEAK, TRANCE, TGF-β, Tpo, Flt-3L, SCF, M-CSF or MSP;
 (v) chemokine (CCL1, CCL2, CCL3, CCL4, CCL5, CCL6, CCL7, CCL8, CCL9/CCL10, CCL11, CCL12, CCL13, CCL14, CCL15, CCL16, CCL17, CCL18, CCL19, CCL20, CCL21, CCL22, CCL23, CCL24, CCL25, CCL26, CCL27, CCL28, CXCL1, CXCL2, CXCL3, CXCL4, CXCL5, CXCL6, CXCL7, CXCL8, CXCL9, CXCL10, CXCL11, CXCL12, CXCL13, CXCL14, CXCL15, CXCL16, CXCL17, XCL1, XCL2 or CX3CL1);

(vi) hormone (progestogens, thyroxine, steroids, insulin, adrenaline Epinephrine, Melatonin, Triiodothyronine, Prostaglandins, Leukotrienes, Prostacyclin, Therocis, Adiponectin, Adrenocorticotropic hormone (or corticotropin), Amylin (or Islet Amyloid Polypeptide), Angiotensinogen and angiotensin, Anti-Müllerian hormone (or Müllerian inhibiting factor or hormone), Antidiuretic hormone (or vasopressin, arginine vasopressin), Atrial-natriuretic peptide (or atriopeptin), Calcitonin, Cholecystokinin, Corticotropin-releasing hormone, Cortistatin, Endothelin, Enkephalin, Erythropoietin, Follicle-stimulating hormone, Galanin, Gastric inhibitory polypeptide, Gastrin, Glucagon, Glucagon-like peptide-1, Gonadotropin-releasing hormone, Guanylin, Hepcidin, Human chorionic gonadotropin, Inhibin, Insulin-like growth factor (or somatomedin), Leptin, Lipotropin, Melanocyte stimulating hormone, Motilin, Orexin, Osteocalcin, Oxytocin, Relaxin, Renin, Secretin, Somatostatin, Thrombopoietin, Uroguanylin, Vasoactive intestinal peptide, estrogen, glucocorticoid, or secosteroid); or (vii) growth factor (G-CSF, GM-CSF, Fas-ligand, Adrenomedullin (AM), Angiopoietin (Ang), Autocrine motility factor, Bone morphogenetic proteins (BMPs), Ciliary neurotrophic factor family, Ciliary neurotrophic factor (CNTF), Leukemia inhibitory factor (LIF), Interleukin-6 (IL-6), Colony-stimulating factor, Macrophage colony-stimulating factor (m-CSF), Granulocyte colony-stimulating factor (G-CSF), Granulocyte macrophage colony-stimulating factor (GM-CSF), Epidermal growth factor (EGF), Ephrin (optionally A1-A5 or B1-B3), Erythropoietin (EPO), Fibroblast growth factor (optionally FGF1-FGF23), Foetal Bovine Somatotrophin (FBS), GDNF family of ligand, Glial cell line-derived neurotrophic factor (GDNF), Neurturin, Persephin, Artemin, Growth differentiation factor-9 (GDF9), Hepatocyte growth factor (HGF), Hepatoma-derived growth factor (HDGF), Insulin, Insulin-like growth factor, Insulin-like growth factor-1 (optionally IGF-1 or IGF-2), Interleukin (optionally IL-1, Cofactor for IL-3 and IL-6, IL-2, IL-3, IL-4, IL-5, IL-6 or IL-7), Keratinocyte growth factor (KGF), Migration-stimulating factor (MSF), Macrophage-stimulating protein (MSP), also known as hepatocyte growth factor-like protein (HGFLP), Myostatin (GDF-8), Neuregulins (optionally NRG1-NRG4), Neurotrophins, Brain-derived neurotrophic factor (BDNF), Nerve growth factor (NGF), Neurotrophin-3 (NT-3), Neurotrophin-4 (NT-4), Placental growth factor (PGF), Platelet-derived growth factor (PDGF), Renalase (RNLS)—Anti-apoptotic survival factor, T-cell growth factor (TCGF), Thrombopoietin (TPO), Transforming growth factor alpha (optionally TGF-α, TGF-β (optionally TGF-β1, TGF-β2, TGF-β3)), Tumor necrosis factor-alpha (TNF-α), or Vascular endothelial growth factor (VEGF)).

11. A method for monitoring a biological event, comprising:
   a. creating, in a microfluidic system, at least one droplet capable of generating a detectable event, said at least one droplet comprising:
      i. at least one single cell;
      ii. one or more first capturing agent, wherein said one or more first capturing agent is capable of binding said at least one single cell as well as a compound of interest; and
      iii. one or more second capturing agent comprising a label, wherein said one or more second capturing agent is capable of binding said compound of interest;
   b. incubating said at least one droplet; and
   c. subjecting said at least one droplet to a direct detection; wherein the presence or relocalization of said detectable event within said at least one droplet is indicative of the presence of said compound of interest, wherein the compound of interest is produced by said at least one single cell, and wherein said at least one or more first capturing agent is bound to said at least one single cell before said at least one droplet is formed.

12. The method according to claim 11, wherein the biological event is an immune response or modulation thereof.

13. A method for detecting a compound of interest in a droplet, comprising:
   a. providing a microfluidic system comprising:
      i. at least one inlet;
      ii. at least one outlet; and
      iii. one or more channels;
   b. injecting in said microfluidic system a stream of droplets, wherein at least one droplet comprises:
      i. at least one single cell;
      ii. a plurality of a first capturing agents capable of binding said at least one single cell as well as said compound of interest; and
      iii. a plurality of second capturing agents, each comprising a label, wherein said plurality of second capturing agents is capable of binding said compound of interest;
   c. incubating said droplets under conditions that allow the production of the compound of interest, whereby if the compound of interest is produced by said at least one single cell, it is capable of being captured by said plurality of first and second capturing agents; and
   d. determining the presence of the compound of interest by detecting a presence or relocalization of said label; wherein said plurality of the first capturing agents is bound to said at least one single cell before said at least one droplet is formed.

14. A microfluidic system comprising:
   a. at least one inlet;
   b. at least one outlet;
   c. one or more channels;
   d. a module for creating at least one droplet comprising:
      i. one or more single cell;
      ii. a first capturing agent; and
      iii. a second capturing agent;
   e. a detection module detecting droplet containing cells producing a compound of interest; and
   f. an analysis module configured for the analysis of a signal; wherein the first capturing agent is bound to at least one of said one or more single cell before the at least one droplet is formed; wherein said first capturing agent is capable of binding said one or more single cell as well as said compound of interest.

15. The microfluidic system according to claim 14, wherein the microfluidic system is used for detection of the compound of interest or monitoring a biological event, by
   a. creating the at least one droplet in said microfluidic system, wherein said-second capturing agent is capable of binding said compound of interest,
   b. incubating said at least one droplet capable of generating a detectable event, c. subjecting said at least one droplet to a direct detection, wherein the presence or relocalization of said detectable event within said at least one droplet is indicative of the presence of said compound of interest.

* * * * *